(12) United States Patent
Sokolowski et al.

(10) Patent No.: US 7,016,036 B2
(45) Date of Patent: Mar. 21, 2006

(54) METHOD FOR PERFORMING A SPECTROSCOPIC ANALYSIS ON A POLYMER SAMPLE, AND RELATED ARTICLES

(75) Inventors: Alex Dimitri Sokolowski, Albany, NY (US); Walter van Kruijsen, Cartagena Murcia (ES)

(73) Assignee: General Electric, Pittsfield, MA (US)

( * ) Notice: Subject to any disclaimer, the term of this patent is extended or adjusted under 35 U.S.C. 154(b) by 120 days.

(21) Appl. No.: 10/445,570

(22) Filed: May 27, 2003

(65) Prior Publication Data

US 2004/0239926 A1 Dec. 2, 2004

(51) Int. Cl.
*G01J 3/42* (2006.01)
(52) U.S. Cl. ............. 356/319; 356/326; 356/402; 356/405
(58) Field of Classification Search ............. 356/300, 356/319, 326, 328, 402, 425
See application file for complete search history.

(56) References Cited

U.S. PATENT DOCUMENTS 4,154,533 A * 5/1979 Levine ................ 356/445
5,087,120 A * 2/1992 Anthony ............... 356/36
5,919,530 A   7/1999 Hurley et al.
6,075,608 A * 6/2000 Feldman et al. ......... 356/406
2004/0065830 A1 * 4/2004 Boon et al. ......... 250/339.11

FOREIGN PATENT DOCUMENTS

EP          1302764 A1 *  4/2003
WO     WO 02/054048 A1 *  7/2002

OTHER PUBLICATIONS

"Measuring Loose Powder Using the LabScan XE", World Wide Web PAGE http://Hunterlab.com/applicationnotes/powder.html; pp. 1-5, Mar. 26, 2003, May 8, 2003.
"Measuring Plastic Pellets Using the LabScan XE", World Wide Web PAGE http://www.Hunterlab.com/application-notes/powder.html; pp. 1-5, Mar. 26, 2003, May 8, 2003.

* cited by examiner

*Primary Examiner*—F. L. Evans

(57) ABSTRACT

A sampling system for performing a spectroscopic analysis on a polymer during its production is described. The system includes a transfer tube capable of transporting the polymer from a production site to a storage site. The tube includes an entry site connected to the production site; and an exit site connected to the storage site. A transparent window is inserted into the wall of the tube, and a door or other barrier is provided to stop the flow of polymer through the tube, so that it accumulates against the window. A spectroscopic device situated outside the tube then takes a reading of the polymer through the window, to perform the desired analysis. Related methods are also described.

19 Claims, 4 Drawing Sheets

METHOD FOR PERFORMING A SPECTROSCOPIC ANALYSIS ON A POLYMER SAMPLE, AND RELATED ARTICLES

BACKGROUND OF THE INVENTION

In a general sense, this invention relates to polymer processing. More specifically, it relates to methods and apparatuses for analyzing spectroscopic properties of the polymer during one of the processing steps.

Plastics, i.e., polymeric resins, are clearly one of the more important materials of use today. Methods for making and using plastics have been well-known for decades. In particular, thermoplastic resins are extremely popular because they can be readily molded into a wide variety of high-quality articles of manufacture. Non-limiting examples of thermoplastic polymers include polycarbonates, polyesters, polyphenylene ethers, styrene resins, acrylic resins, acrylonitrile-butadiene-styrene (ABS) resins, polyamides, polyetherimides, polyphenylene sulfide resins, and various combinations (e.g., copolymers) thereof.

The polymer resins are usually compounded and manufactured as pellets or powders that can be easily shipped to a customer, and/or stored for later processing. In a typical process for many thermoplastics, the base polymer (or multiple polymers) is combined with various other additives in a mixer or extruder. The blended material is then extruded into a water bath, and pelletized. The pellets are then dried in one or more drying operations, and sent to bins for storage, or shipment to a custom molder.

During production, polymer materials often have to be analyzed for a variety of specified characteristics. They include: composition, color, thermal properties, tensile and flexural properties; residual monomer levels, molecular weight, and particle size. The composition and color of the polymer are usually determined by spectroscopic means.

Very often, the color of a polymer is critical for aesthetic appeal, or for properly identifying the particular brand of articles made from the polymer. A desired color for the polymer is usually achieved by incorporating selected pigments and/or colorants into the polymer blend. Great care must be taken to make sure the color matches a specified standard. In these instances, procedures for determining the precise color during polymer processing must be in place.

In a conventional processing system for colored polymers, an operator usually must draw a sample of the polymer as it is extruded, and take it to a laboratory. The sample must then be molded into one or more test plaques. Color measurements are then taken on the plaques, using a calorimeter, for example. If the color conforms to the specification, a signal is given to continue production. If the color is out of specification, the blended polymer mixture must be adjusted (e.g., adjustment of the colorant levels). The reformulated polymer product is then tested again for conformance to the color standard, and the process continues.

While the conventional system for the color-sampling of polymers is adequate in many instances, it is accompanied by some drawbacks. For example, critical production time can be wasted while a sample is drawn and tested in a laboratory. (The polymer extrusion line may have to be slowed down or shut-down during this step). Moreover, the conventional system is at times labor-intensive. For example, one or more individuals may be needed to handle the actual sampling and testing, while additional manpower is required to monitor the production line while the sample is being evaluated. For large-scale polymer production lines, a disruption in the continuity of the overall process can be economically undesirable.

With these concerns in mind, new methods and systems for efficiently carrying out the spectroscopic analysis of a polymer sample would be welcome in the art. The methods should be capable of performing the analysis "on-line", so that very little production time is lost during the procedure. Moreover, the methods should provide a spectroscopic analysis which generally is as accurate as the analysis performed off-line, e.g., on a test plaque in a laboratory. Furthermore, the methods and accompanying apparatus should be compatible with the other production and processing operations, e.g., drying, pelletizing, and storage operations.

BRIEF DESCRIPTION OF THE INVENTION

A primary embodiment of this invention is directed to a sampling system for performing a spectroscopic analysis on a polymer during its production. The sampling system comprises:

a transfer tube through which the polymer moves from one site to another site, wherein the tube comprises barrier means for controllably blocking polymer movement, and further comprises a tube wall in which a window or other transparent plate is situated, so that the polymer can be pressed against the window when polymer movement through the tube is blocked; and a spectroscopic device located outside the transfer tube, and positioned so that a spectroscopic measurement for the polymer can be made through the window.

In some specific embodiments, the sampling system comprises:

a) a transfer tube capable of transporting the polymer from a production site to a storage site, wherein the tube comprises:
  I) a tube wall with an inner surface and an outer surface;
  II) an entry site which communicates with the production site;
  III) an exit site which communicates with the storage site; and
  IV) a transparent plate which forms a portion of the tube wall, having an inner surface and an outer surface which are substantially co-extensive with the tube wall;

b) barrier means for preventing the polymer (e.g., polymer pellets) from flowing through the exit site to the storage site, thereby allowing the sample to accumulate within the transfer tube and to be contained against the inner surface of the transparent plate; and c) a spectroscopic device, positioned in a location exterior to the transfer tube, so that an energy beam emitted from the device can be aimed at a portion of the polymer through the transparent plate of the transfer tube.

A number of spectroscopic devices can be employed with this invention, and are described below. While calorimeters and other types of spectrophotometers are typically used, spectroscopic devices which determine other properties, like polymeric composition, are also possible.

The transparent plate which contains and supports the polymeric sample can be a glass or plastic window. Moreover, the transfer tube can constitute a portion of an entire polymer production system. Various polymers manufactured in this system are described below, e.g., polycarbonates and polycarbonate blends. Thus, a method for performing an on-line spectroscopic analysis of a polymer product during manufacturing represents another embodiment of this invention.

Other features and advantages of the present invention will be apparent from the following, detailed description, taken in conjunction with the drawings.

DETAILED DESCRIPTION OF THE INVENTION

Figure 1:
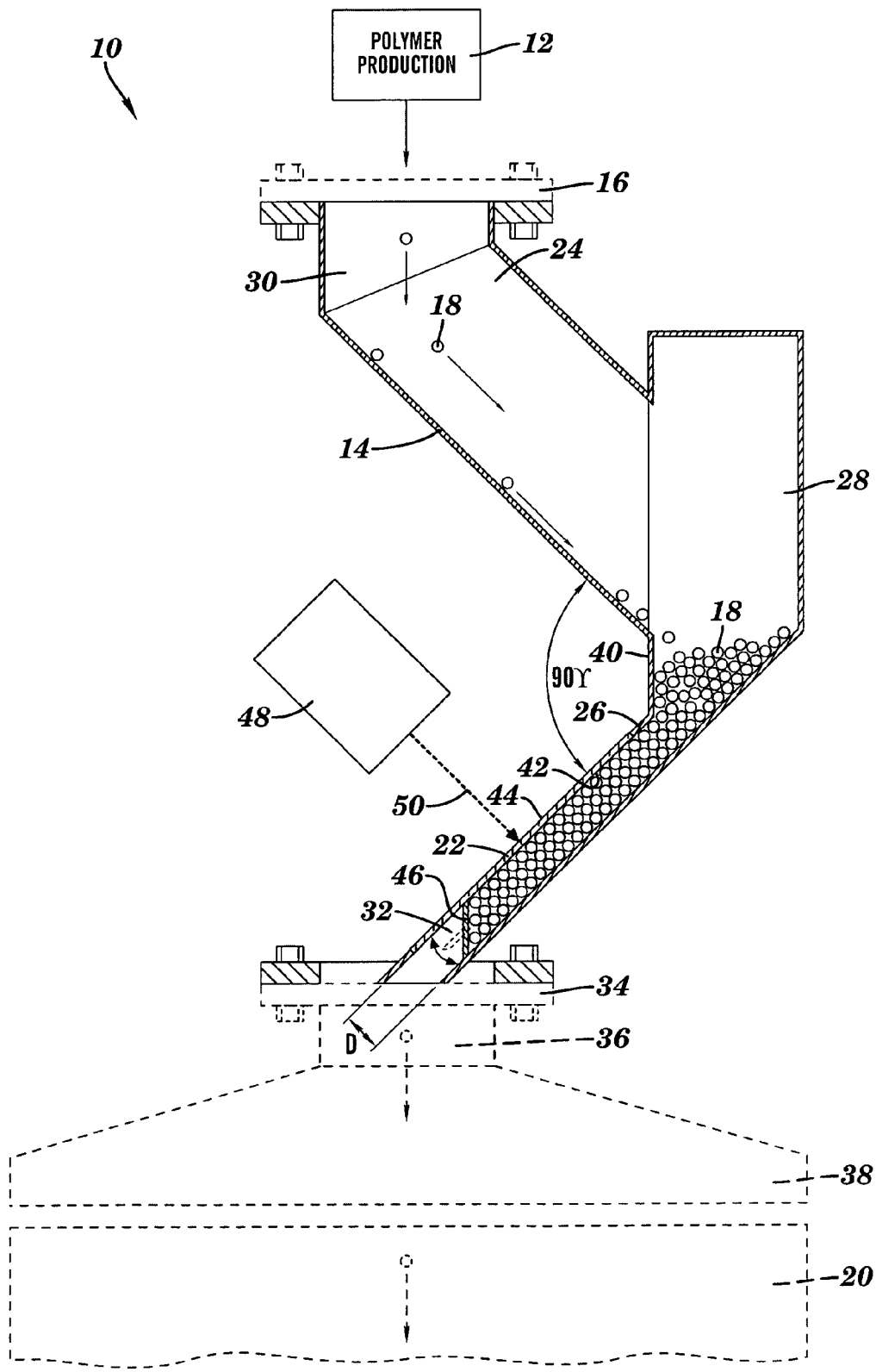
FIG. 1 is a cross-sectional side-view of a sampling apparatus according to this invention.

With reference to FIG. 1, a primary embodiment of the sampling apparatus 10 of this invention is incorporated into a polymer production operation 12. Operation 12 can include many individual steps, all known to chemical engineers working in the industry. Usually, resinous components, additives, and other conventional ingredients are first combined and then directed to the heated barrel (or barrels) of an extruder. The blended polymeric material, in the form of strands, is extruded into a water bath. After being cooled in the water bath, the strands of polymer are chopped into pellets in a pelletizer. Water is then removed from the pellets in one or more drying operations.

As described in U.S. Pat. No. 5,919,530, the term "pellets" is meant to encompass various geometric forms, such as squares, trapezoids, cylinders, lenticular shapes, cylinders with diagonal faces, flakes, and chunks. The term also is meant to embrace substantially spherical shapes, including particles of powder, and larger-size spheres. While the polymer material is often sold as pellets, it could be in any shape or size suitable for use in the equipment employed to form the final article. U.S. Pat. No. 5,919,530 is incorporated herein by reference.

In a conventional operation, the dried polymer pellets would typically be gravity-fed through a pipe or tube to one or more bins, for storage or shipment to a customer. In an embodiment of the present invention, the pellets are directed into transfer tube 14 through entry site 16. (In this description, the word "tube" is used for simplicity, but is not meant to be shape-restrictive. The indicated passageway/conduit could be in other shapes as well, e.g., rectangular, conical, and the like). The transfer tube is made from conventional materials deemed suitable for resin production systems, e.g., steel, aluminum, reinforced plastics, and the like. There is also no special requirement for entry site 16; it is usually a conventional coupling mechanism suitable for attachment to the conduit through which the pellets are fed.

Transfer tube 14 can have various shapes and sizes, depending on several factors. First, the tube must have a shape which efficiently directs the polymer product 18 to its final destination, e.g., storage site 20. The tube must also have a diameter large enough to permit sufficient flow of the polymer to the storage site when the flow is not being interrupted for spectroscopic analysis. Moreover, however, the shape and size of the tube must be sufficient to allow polymer product 18 to rapidly accumulate and be contained against transparent window 22 (discussed below), when polymer flow is purposefully interrupted.

In the embodiment of FIG. 1, transfer tube 14 is angled or bent in a manner appropriate for these factors. Thus, the tube includes upper section 24 and lower section 26. A reservoir 28 is situated between the upper section and the lower section, in effect, joining them. Upper section 24 can be connected to entry site 16 by segment 30. However, the upper section could just as readily be directly connected to entry site 16 if it were shaped appropriately. The lower terminal portion 32 of lower section 26 can be connected to exit site 34 by any convenient means. Alternatively, terminal portion 32 can be freely positioned within an open area 36 which constitutes the uppermost portion of enclosure hood or "bell" 38.

The bending angle between upper section 24 and lower section 26 is depicted in the figure as being approximately 90°. However, the bending angle can vary considerably, depending on various factors. They include: available space for the transfer tube; the length and diameter of the tube (and its individual sections); the desired flow rates for the polymer product, polymer pellet size, and material bulk viscosity. Frequently, a bending angle is selected which is sufficient to generally keep the terminal stage of the production site in substantially vertical alignment with the storage site.

In this embodiment, transparent plate or window 22 is incorporated into the lower section 26 of the transfer tube. (The plate could have been located in other sections of the transfer tube, e.g., upper tube section 24. However, location of the plate within the lower section is more convenient in a gravity-fed polymer flow system). The plate forms a portion of the tube wall 40. The plate has an inner surface 42 and an outer surface 44 which are substantially coextensive with tube wall 40. In other words, the plate preferably (but not necessarily) has a contour similar to the contour of the tube.

Window 22 can be made of any transparent material, as long as the material does not significantly affect the passage of the spectroscopic beam. (For example, the material should not reflect or diffract the beam to a degree which would impede the spectroscopic measurement). Non-limiting examples of the window material include glass, as well as various plastics. Examples of the plastics are polycarbonate (e.g., LEXAN® polycarbonate) and acrylic materials, e.g., poly(methyl methacrylate) polymers. The size of the window will depend in part on the type of spectroscopic instrument, as well as its position. Usually, the window should have a surface area sufficient to permit the passage of one or more spectroscopic energy beams (described below) onto the portion of the polymer required for the analysis. In the case of a spectrophotometer in an industrial setting, the window may have a size as great as about 15 cm×30 cm.

The thickness of window 22 will also vary according to several factors, such as its composition and size, and the type of spectroscopic instrument employed. The window should be thick enough to provide support for the polymeric material which will be contained against it, without significant bending (in the case of plastic). However, it should not be so thick as to adversely affect the spectroscopic beam. Usually, the window will have a thickness in the range of about 100 mm to about 500 mm. The window can be attached to transfer tube section 24 by any convenient means. For example, it can be bolted, clamped, or welded (e.g., within a frame) to the tube section.

As alluded to previously, polymer flow through the transfer tube is selectively shut off by any type of barrier means. As illustrated in FIG. 1, one type of barrier can be a door 46.

The door is situated within or adjacent to the lower, terminal portion 32 of lower tube section 26. The exact location of the door is not critical, as long as it can be controllably opened and closed. (In the figure, the door is depicted in its closed position, with the open position depicted in phantom). Any conventional device (not shown) for controlling the movement of the door is possible, e.g., pneumatic means or mechanical means. When the door is open, normal polymer flow through exit site 34 to storage site 20 is unimpeded.

Although a door is described in the present disclosure, various other types of barriers can serve the same purpose. For example, a lower portion of transparent plate 22 could be left detached from the tube wall, and be "bent" into the passageway of the transfer tube when polymer flow had to be stopped. Moreover, other types of barriers or obstructions could be used. For example, some sort of plate could be inserted into a cross-section of the tube through cut-out slots in the tube. Those skilled in the art may be able to readily devise other barriers which generally perform the same function, and are included within this inventive concept.

When door 46 is closed, polymer pellets 18 are prevented from flowing through the exit site to the storage site. Instead, the polymer accumulates in lower tube section 26, backing up into reservoir 28. The shape and size of the reservoir can vary greatly. Its primary purpose is to accommodate excess polymer. This serves to prevent the polymer from backing up fully into upper tube section 24 during the closed-door stage, where it could perhaps interfere with the polymer production operation.

The shape and size of lower tube section 26 can also vary considerably. The tube should have a diameter "D" which is small enough to allow polymer pellets 18 to quickly accumulate therein, and press against the inner surface 42 of transparent plate 22. In this manner, a spectroscopic analysis can be undertaken very quickly, e.g., within about 0.5 second to about 60 seconds after door 46 has been closed. However, lower tube section 26 should have a diameter large enough to permit efficient flow of the polymer during normal operation, i.e., when the door has been opened. For a large-scale polymer production operation, the diameter of the lower tube section might vary from about 2 inches (5 cm) to about 4 inches (10 cm).

As alluded to above, filling of lower tube section 26 with polymer pellets 18 causes the pellets to be pressed against transparent plate 22. (The pressure against the plate is relatively small, i.e., not great enough to compress the pellets themselves). In this manner, the energy beam of the spectroscopic device (discussed below) can be directed against a relatively flat, smooth, and uniform surface of polymer product. Such a receiving-surface is highly desirable for many spectroscopic tests, e.g., color measurements. The uniformity of the surface minimizes inaccurate instrument readings due to light-scattering, surface shadows, and the like.

After lower tube section 26 is substantially filled with polymer, one or more spectroscopic measurements can be taken by way of spectroscopic device 48. As mentioned above, a number of different types of devices can be used, depending on the polymer properties being analyzed. Examples of the properties which are typically analyzed are composition, color, residual monomer levels, additive levels, particle size, molecular weight, byproduct composition, and contaminant composition. Non-limiting examples of spectroscopic devices are as follows: calorimeters, spectrophotometers, NMR spectrometers, FTIR spectrometers, Raman spectrometers, X-Ray fluorescence spectrometers, IR spectrometers, and Near IR spectrometers. In general, they are all commercially available. (NMR and FTIR spectrometers are often used for compositional analysis, e.g., polymer structure).

Spectroscopy and spectroscopic devices are described in many references. Examples include "The Encyclopedia Americana—International Edition" (Grolier Incorporated, 1981), Volume 6, pp. 389–390); and Volume 25, pp. 466 et seq.; and Kirk-Othmer "Encyclopedia of Chemical Technology", Fourth Edition (1993), Volume 6, pp. 859–860 et seq. These texts are incorporated herein by reference. Various spectroscopic devices are also discussed in U.S. Pat. Nos. 4,690,954; 5,468,259; 6,294,647; 6,331,580; 6,482,916; 6,508,984; 6,512,056; 6,518,340; 6,518,378; and 6,521,714, which are also incorporated herein by reference.

The particular location of spectroscopic device 48 can vary considerably, and depends in large part on the type of device being used. Those skilled in the field of analytical instrumentation are very familiar with the positioning of the instruments, relative to a sample being analyzed. The device usually directs an energy beam 50 to the sample. (Multiple energy beams may be used, e.g., a second beam as a reference). The energy beam can be in the form of light (e.g., ultraviolet light), heat, or other forms, such as x-rays and microwaves. In a typical scenario, the energy beam contacts the sample. A reflected or resultant (e.g., modified) beam or other energy form, which is characteristic of a particular property of the polymer sample, then returns to the spectroscopic device for analysis.

In some embodiments of this invention, color measurement of the polymer sample is the primary objective. Well-known standards exist for light transmission and color measurement, e.g., ASTM D-1003. As alluded to above, spectrophotometers are typically used for color determination. For the purpose of this disclosure, the term "spectrophotometer" is meant to also include spectrocolorimeters and colorimeters. However, calorimeters are sometimes considered to be a separate class of instrument.

The spectrophotometers are often used for industrial color control functions; they are sometimes referred to as "tristimulus calorimeters". Many models are commercially available. Examples include the Hunterlab Tristimulus Colorimeter, Model D25 P-9; and the Gardner XI-835 Colorimeter. Different color scales can be used. Examples include the Hunter "L,a,b" scale (described below), as well as the CIE color system, which utilizes X, Y, Z primaries to define all colors in a color space.

In the present instance, spectrophotometer 48 can emit (or "flash") a light beam 50, which travels through transparent plate 22, and contacts a portion of polymer sample 18. The contact area will vary with the type of spectrophotometer, but is often a circle having a diameter in the range of about 1 cm to about 15 cm. The reflected beam which returns to the spectrophotometer provides the color measurement, according to the particular instrument's mechanism.

An operator can then review the color measurement, and determine if the color is within a required specification. If the color is acceptable, door 46 can be opened. The polymer pellets then continue to flow through exit site 34 into site 20, e.g., a bin, conduit, or other type of vessel, for further processing and/or shipment to a customer. If the color is not acceptable, the door may remain closed, and/or the polymer pellets may be diverted to another bin for disposal, or for storing surplus material. The appropriate change in color ingredients (e.g., via pigment feeders) is then made in the polymer production operation, to correct the variance in color. Another spectroscopic analysis can then be undertaken on the modified material, to determine if it now has the proper color.

As alluded to above, the present invention is especially useful for continuous extrusion systems. In these systems, the polymer components being blended are continuously fed into extruders, along with the colorants and other ingredients. In the past, stopping a continuous production operation for any extended period of time to carry out analytical tests could represent a serious problem—especially if the operation is capacity-constrained. However, with the "stop-flow" system described herein, the flow of polymer product is only momentarily halted, to allow a fast, accurate spectroscopic determination. The processing operation can then be quickly resumed, once the product is determined to be within specification.

EXAMPLES

The examples which follow are merely illustrative, and should not be construed to be any sort of limitation on the scope of the claimed invention.

A polymer product based on a blend of polycarbonate and acrylonitrile-butadiene-styrene (ABS) was prepared according to a conventional process, e.g., compounding of the ingredients, followed by extrusion. The product was provided with a designated color (blue-1683), by incorporation of an appropriate pigment. The polymer was extruded into a water bath, pelletized, and then dried, according to conventional procedures alluded to previously.

Samples of the dried polymer pellets were taken to an injection molding machine, and molded into test plaques. The plaques were inserted into a laboratory spectrophotometer (Model 7000A from Greta Macbeth). The spectrophotometer produced a set of color values for each sample, according to the Hunter "L, a, b" scale. For such a scale, the "a" value measures green-to-red; the "b" value measures yellow-to-blue; and the "L" value measures white-to-black.

Additional polycarbonate/ABS product was prepared according to the same general process, i.e., compounding, extrusion into a water bath, pelletization, and drying. After drying, however, these pellets were directed through an on-line, stop-flow system similar to that depicted in FIG. 1. The transfer tube was rectangular in shape, and made of steel. It included the upper and lower sections, along with the reservoir. The upper section had a diameter of about 50 cm and a length of about 0.5 meter, while the lower section had a diameter of about 6 cm and a length of about 0.3 meter. Upper and lower sections were positioned at about 90° relative to each other, as indicated in the FIG. 1. The reservoir at the junction of the two sections had a square base of about 15 $cm^2$, with a height of about 60 cm.

The transparent plate or window in the lower section of the transfer tube was made from LEXAN® polycarbonate. It had a thickness of about 0.6 cm, a length of about 30 cm, and a width of about 10 cm. The plate was fastened to a cut-out section of the tube by two thumb-screws that were placed onto bolts that extended through cut-out slats, to allow for height positioning.

An Xrite® spectrophotometer, Teleflash model, was used as the spectroscopic device. It was positioned on a platform, about 0.45 meter away from the transparent plate. The exit beam of the spectrophotometer was adjusted to ensure that it would focus on a location in the approximate center of the transparent plate.

The polymer pellets had a size in the range of about 2–6 mm. The pellets were allowed to flow into the sampling system. In this particular example, a door was not used to stop the flow of pellets, as depicted in FIG. 1. Instead, the lower portion of transparent plate 22, which was left detached from the tube wall, served as the door. At a desired time, a mechanical arm outside the tube put pressure on the detached portion of the door, forcing it to move into the tube and thereby block the passage and shut off the flow of pellets. The pellets then filled up the lower tube section and backed up into the reservoir. The lower tube section was completely filled in about 7 seconds.

At that point, the spectrophotometer was activated. Its spectroscopic beam made contact with the polymer sample through the window, and automatically produced a set of the "L, a, b" color values for the sample. The door at the exit site was then opened, and polymer flow into a receiving bin was allowed to continue. Over a series of test runs, the average time period between closing the door and re-opening it was as little as about 15 seconds.

Figure 2:
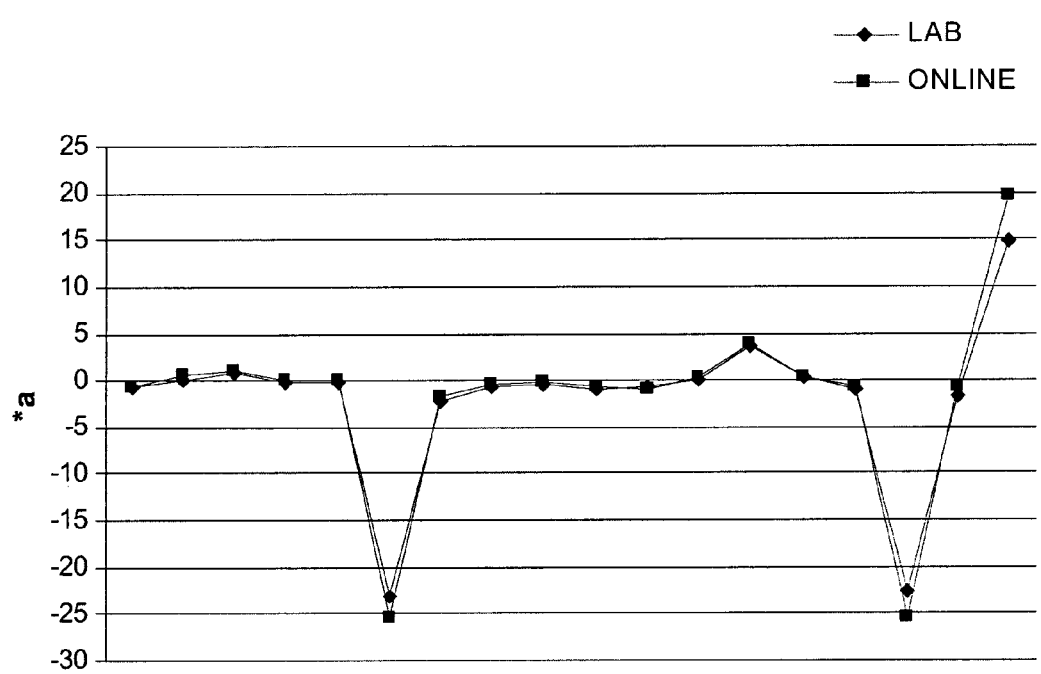
FIG. 2 is a graphical representation of a set of spectroscopic data points for a polymeric sample.

FIG. 2 is a graphical representation of spectroscopic data points for the "a" parameter on the Hunter scale. (For FIG. 2, as well as FIGS. 3 and 4, the points on the x-axis represent a "measurement occurrence", corresponding to the measurements taken for the respective "L, a, b" color parameters). Separate curves for the laboratory measurements and the on-line measurements are provided. It's clear from the figure that the curves are substantially identical to each other, demonstrating very good correlation between the laboratory measurement and the on-line measurement.

Figure 3:
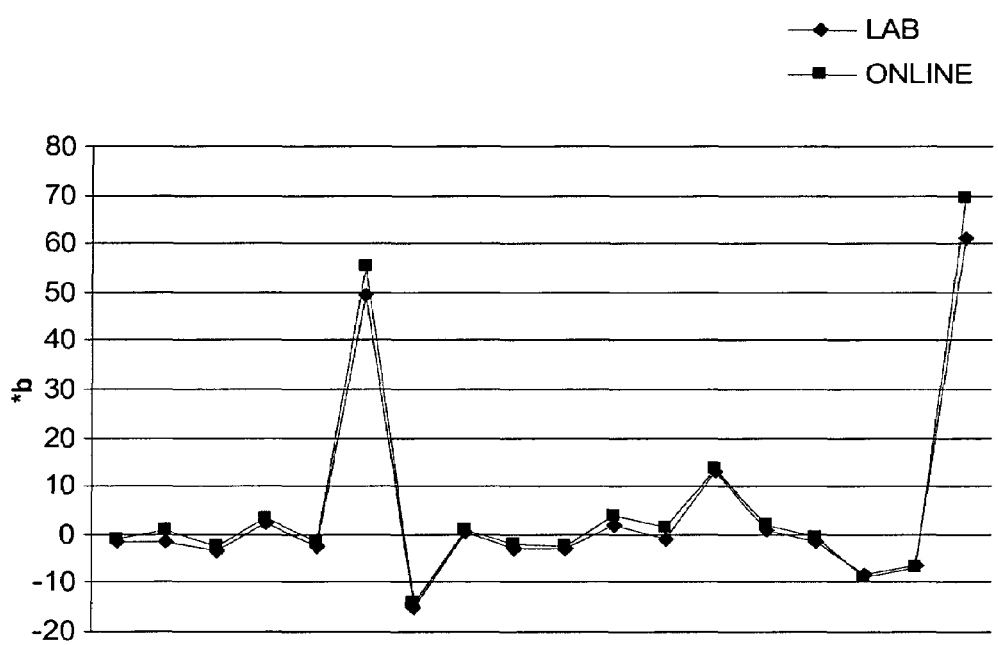
FIG. 3 is a graphical representation of a another set of spectroscopic data points for the polymeric sample.

FIG. 3 is a graph of the spectroscopic data points for the "b" parameter on the Hunter scale. Again, separate curves are provided for the laboratory measurements and the on-line measurements. These curves are also substantially identical.

Figure 4:
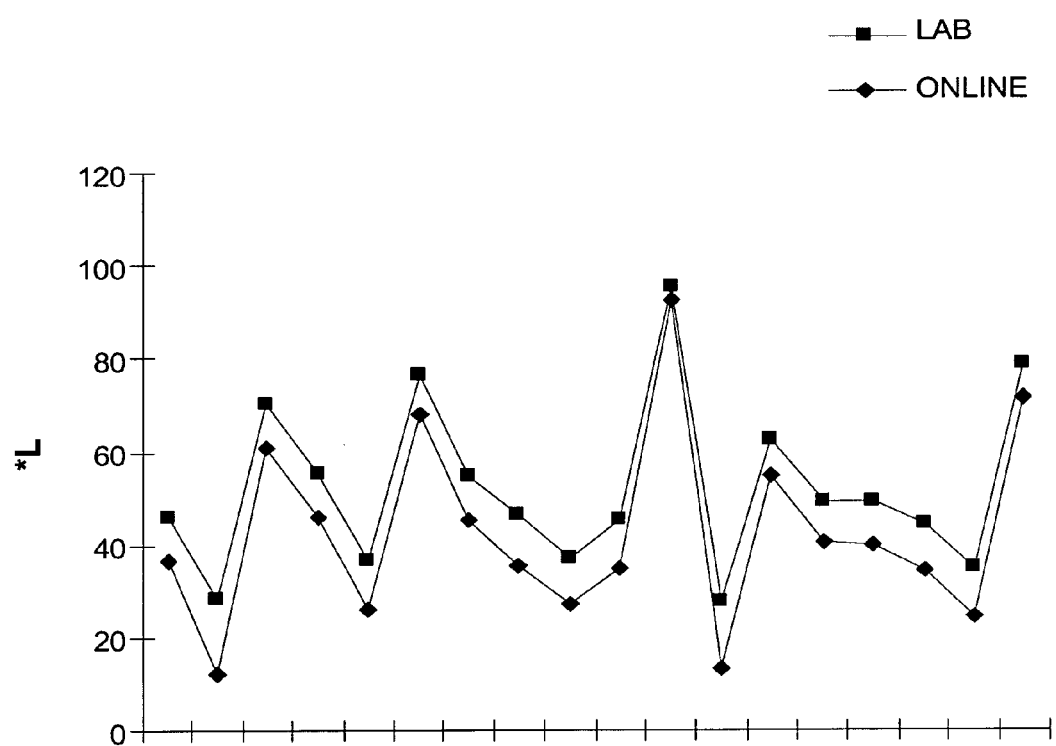
FIG. 4 is a graphical representation of a third set of spectroscopic data points for the polymeric sample.

FIG. 4 is a graph of the spectroscopic data points for the "L" parameter on the Hunter scale. For these particular samples, there is a difference in the spectroscopic values for the laboratory measurements, as compared to the on-line measurements. However, the difference is generally consistent, point-to-point. Thus, for a particular sample of colored polymer, the on-line reading could be easily calibrated against a standard, laboratory reading, to provide accurate color determination for the material passing through the sampling system.

This invention has been described according to specific embodiments and examples. However, various modifications, adaptations, and alternatives may occur to one skilled in the art without departing from the spirit and scope of the claimed inventive concept. All of the patents, articles, and texts which are mentioned above are incorporated herein by reference.

What is claimed:

1. A sampling apparatus for performing a spectroscopic analysis on a polymer during its production, comprising:
   a) a transfer tube capable of transporting the polymer from a production site to a storage site, wherein the tube comprises:
      I) a tube wall with an inner surface and an outer surface;
      II) an entry site which communicates with the production site;
      III) an exit site which communicates with the storage site;
      IV) a transparent plate which forms a portion of the tube wall, having an inner surface and an outer surface which are substantially co-extensive with the tube wall;

b) barrier means for preventing the polymer from flowing through the exit site to the storage site, thereby allowing the polymer to accumulate within the transfer tube, and to be contained against the inner surface of the transparent plate; and c) a spectroscopic device, positioned in a location exterior to the transfer tube, so that an energy beam emitted from the device can be aimed at a portion of the polymer through the transparent plate of the transfer tube.

2. The apparatus of claim 1, wherein the spectroscopic device is selected from the group consisting of colorimeters, spectrophotometers, NMR spectrometers, FTIR spectrometers, Raman spectrometers, X-Ray fluorescence spectrometers, IR spectrometers, and Near IR spectrometers.

3. The apparatus of claim 1, wherein the spectroscopic device is a spectrophotometer, and the spectroscopic analysis comprises color-determination.

4. The apparatus of claim 1, wherein the spectroscopic device is an NMR spectrometer or an FTIR spectrometer, and the spectroscopic analysis comprises a compositional analysis.

5. The apparatus of claim 1, wherein the transparent plate has a surface area sufficient to permit the passage of the energy beam onto the portion of the polymer required for the spectroscopic analysis.

6. The apparatus of claim 5, wherein the transparent plate comprises glass or plastic.

7. The apparatus of claim 6, wherein the plastic is a polycarbonate or acrylic material.

8. The apparatus of claim 1, further comprising a reservoir within the transfer tube, capable of accommodating excess polymer while the spectroscopic analysis is undertaken.

9. The apparatus of claim 1, wherein the transfer tube comprises an upper section and a lower section joined to the upper section at an angle, so that continuous polymer flow can be maintained through the tube, while the production site and the storage site are vertically aligned with one another.

10. The apparatus of claim 1, wherein the barrier means for preventing the polymer from flowing through the exit site to the storage site comprises a door.

11. An apparatus for making on-line color measurements on pellets of a polycarbonate blend, comprising:

a) a transfer tube capable of transporting the polycarbonate blend from a production site to a storage site, wherein the tube comprises:
 I) a tube wall;
 II) an entry site which communicates with the production site;
 III) an exit site which communicates with the storage site;
 IV) a transparent glass or plastic plate which forms a portion of the tube wall, having an inner surface and an outer surface which are substantially co-extensive with the tube wall;

b) a door which is capable of preventing the pellets from flowing through the exit site to the storage site, thereby allowing the pellets to accumulate within the transfer tube and to be contained against the inner surface of the transparent plate; and c) a spectrophotometer, positioned in a location exterior to the transfer tube, so that an energy beam emitted from the device can be aimed at a portion of the pellets through the transparent plate of the transfer tube.

12. An apparatus for performing a spectroscopic analysis on a polymer, comprising:

a transfer tube through which the polymer moves from one site to another site, wherein the tube comprises barrier means for controllably blocking polymer movement, and further comprises a tube wall in which a window is situated, so that the polymer can be pressed against the window when polymer movement through the tube is blocked, said apparatus further including a spectroscopic device located outside the transfer tube, and positioned so that a spectroscopic measurement for the polymer can be made through the window.

13. A method for performing a spectroscopic analysis on a polymer being transported from a first location to a second location along a transportation route which comprises a transfer tube, comprising the following steps:

(i) accumulating a portion of the polymer against a first surface of a transparent plate which forms a portion of a wall of the transfer tube; and then (ii) directing an incident energy beam from a spectroscopic device through the plate, from a second surface of the plate substantially opposite the first surface, wherein the energy beam contacts the polymer; and a reflected or resultant beam of energy characteristic of a selected property of the polymer returns to the spectroscopic device for analysis.

14. The method of claim 13, wherein the first location is a polymer production operation, and the second location is a storage site.

15. The method of claim 13, wherein the transparent plate comprises glass or plastic.

16. The method of claim 13, wherein the spectroscopic device is a spectrophotometer, and the spectroscopic analysis comprises color determination.

17. The method of claim 13, wherein the polymer is selected from the group consisting of polycarbonates, polyesters, polyphenylene ethers, styrene resins, acrylic resins, acrylonitrile-butadiene-styrene (ABS) resins, polyamides, polyetherimides, polyphenylene sulfide resins, and combinations of any of the foregoing.

18. A method for manufacturing a polymeric material having a designated color according to a color specification, comprising the following steps:

A) forming a mixture in an extruder, wherein the mixture comprises the polymeric material and one or more colorants and pigments which are sufficient to provide the specified color;

B) extruding and cooling the formed mixture of polymeric material;

C) chopping the extruded polymeric material into pellets;

D) transporting the pellets to a transfer tube which comprises a tube wall having a window incorporated therein;

E) positioning a portion of the pellets against the window;

F) directing at least one incident light beam from a spectrophotometer outside the transfer tube, through the window, so as to contact the pellets and determine the color thereof;

G) (i) verifying that the determined color satisfies the color specification, and then transporting the pellets through the transfer tube to a bin; or (ii) verifying that the determined color does not satisfy the color specification; changing the mixture of step (A) to satisfy the color specification as determined by carrying out step (F) again; and then transporting the pellets, having the satisfied color specification, through the transfer tube to the bin.

19. The method of claim 18, wherein step (B) comprises continuous extrusion.

* * * * *

UNITED STATES PATENT AND TRADEMARK OFFICE
CERTIFICATE OF CORRECTION

PATENT NO. : 7,016,036 B2
APPLICATION NO. : 10/445570
DATED : March 21, 2006
INVENTOR(S) : Sokolowski et al.

Page 1 of 1

It is certified that error appears in the above-identified patent and that said Letters Patent is hereby corrected as shown below:

Column 4,
Line 52, after "15", delete "cmx30" and insert therefor --cm x 30--.

Column 5,
Line 64, after "follows:", delete "calorimeters" and insert therefor --colorimeters--.

Column 6,
Line 37, after "However", delete "calorimeters" and insert therefor --colorimeters--.
Lines 41-42, after "tris-timulus", delete "calorimeters" and insert therefor --colorimeters--.

Signed and Sealed this

Sixth Day of March, 2007

JON W. DUDAS
*Director of the United States Patent and Trademark Office*